(12) United States Patent
Coe

(10) Patent No.: US 8,195,330 B2
(45) Date of Patent: Jun. 5, 2012

(54) INTERACTIVE MEDICINE ORGANIZER

(75) Inventor: Matthew Coe, Annandale, NJ (US)

(73) Assignee: One World Design & Manufacturing Group, Ltd., Warren, NJ (US)

( * ) Notice: Subject to any disclaimer, the term of this patent is extended or adjusted under 35 U.S.C. 154(b) by 70 days.

(21) Appl. No.: 12/802,015

(22) Filed: May 27, 2010

(65) Prior Publication Data

US 2010/0305749 A1    Dec. 2, 2010

Related U.S. Application Data

(60) Provisional application No. 61/217,608, filed on Jun. 2, 2009.

(51) Int. Cl.
*G06F 17/00* (2006.01)

(52) U.S. Cl. ........ 700/243; 700/240; 700/242; 700/244; 700/232

(58) Field of Classification Search .................. 700/231, 700/232, 236, 242–243, 240, 244
See application file for complete search history.

(56) References Cited

U.S. PATENT DOCUMENTS

| | | | |
|---|---|---|---|
| 5,678,571 A * | 10/1997 | Brown | 128/898 |
| 5,710,551 A * | 1/1998 | Ridgeway | 340/870.09 |
| 6,507,275 B2 * | 1/2003 | Romano et al. | 340/309.16 |
| 6,529,446 B1 * | 3/2003 | de la Huerga | 368/10 |
| 7,147,127 B2 | 12/2006 | Lepke et al. | |
| 7,182,218 B2 | 2/2007 | Raines | |
| 2002/0000917 A1 | 1/2002 | Rubenstein | |
| 2004/0158349 A1 * | 8/2004 | Bonney et al. | 700/231 |
| 2006/0180600 A1 * | 8/2006 | Talyor | 221/87 |
| 2008/0119958 A1 * | 5/2008 | Bear et al. | 700/244 |
| 2008/0300719 A1 * | 12/2008 | Duke | 700/244 |
| 2009/0281657 A1 * | 11/2009 | Gak et al. | 700/242 |
| 2009/0306818 A1 * | 12/2009 | Slagley et al. | 700/232 |
| 2011/0022224 A1 * | 1/2011 | Park | 700/232 |

* cited by examiner

*Primary Examiner* — Michael K Collins
(74) *Attorney, Agent, or Firm* — Mitchell J. Mehlman, Esq.

(57) ABSTRACT

Interactive medicine organizers comprising integrated software and hardware elements and multifunctional interactive wireless devices to provide assistance to individuals who need to organize or monitor the administration of one or more medications are provided.

12 Claims, 20 Drawing Sheets

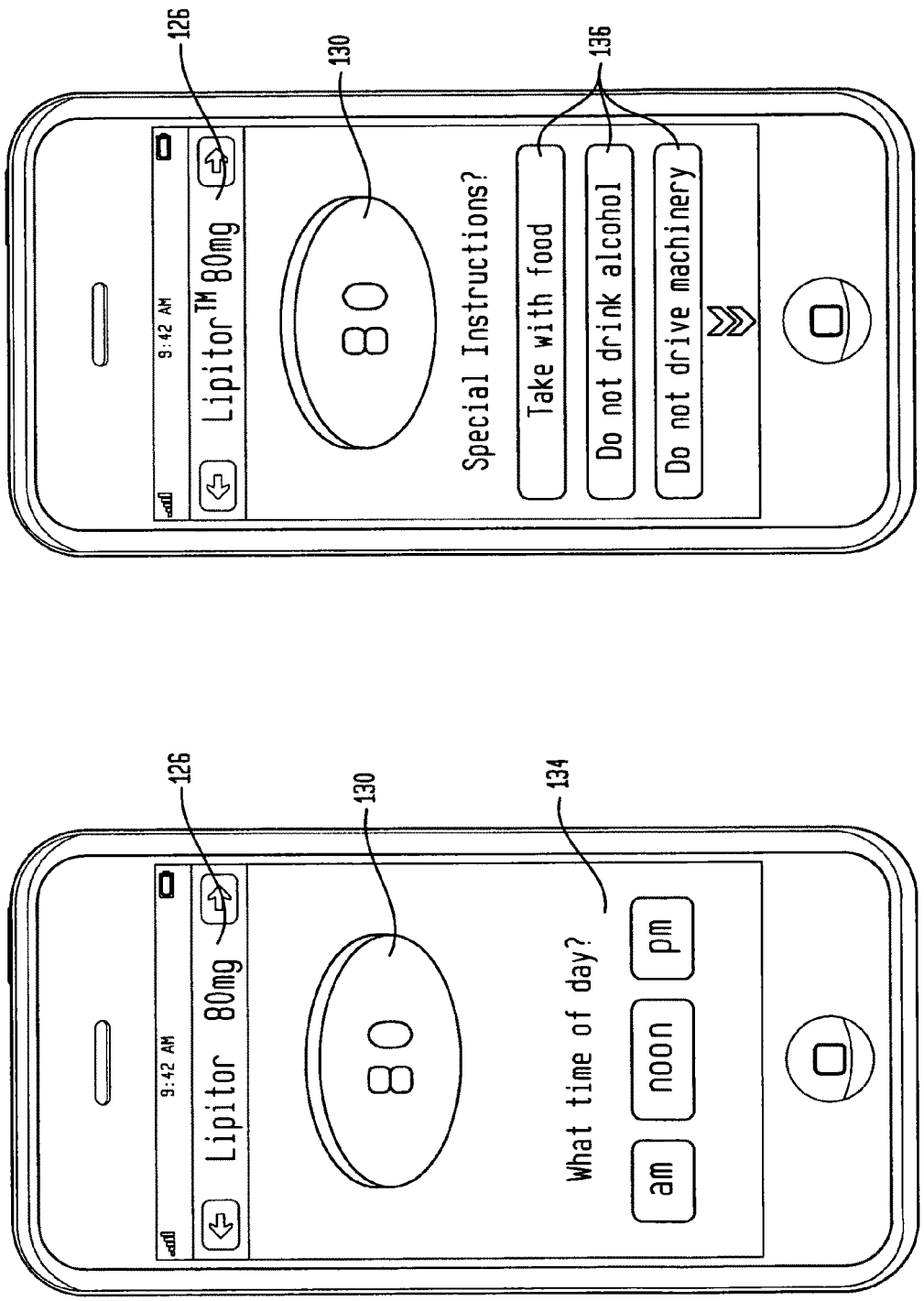

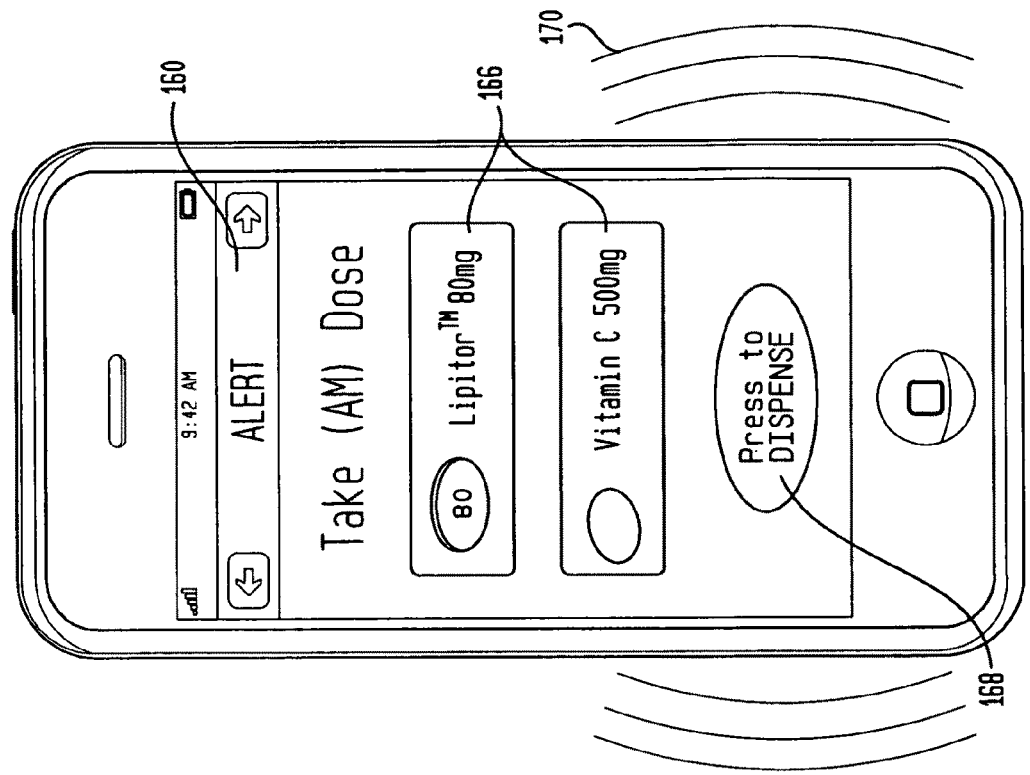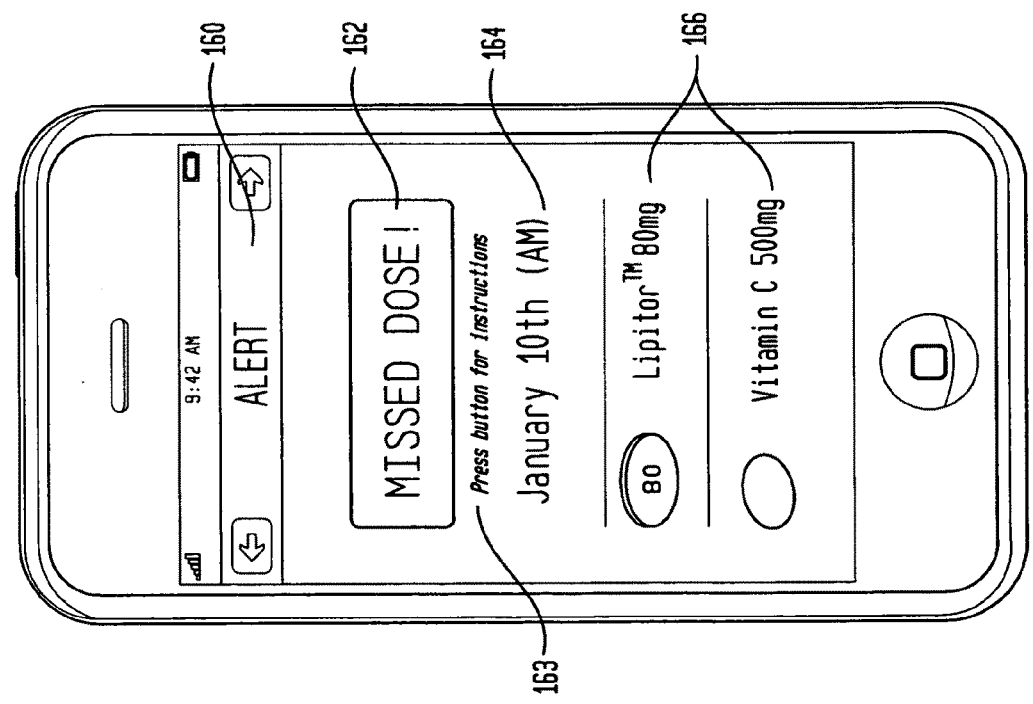

INTERACTIVE MEDICINE ORGANIZER

CROSS-REFERENCE TO RELATED APPLICATION

This application claims priority of U.S. Provisional Application Ser. No. 61/217,608, titled "INTERACTIVE MEDICINE ORGANIZER", filed Jun. 2, 2009, the disclosure of which is incorporated herein by reference in its entirety.

STATEMENT REGARDING FEDERALLY SPONSORED RESEARCH OR DEVELOPMENT

Not Applicable

REFERENCE TO SEQUENCE LISTING, A TABLE, OR A COMPUTER PROGRAM LISTING COMPACT DISC APPENDIX

Not Applicable

BACKGROUND OF THE INVENTION

The present invention relates to interactive medicine organizers (IMOs) including multifunctional interactive wireless devices that can communicate with one or more dispensers to dispense medications and methods for monitoring and increasing patient compliance with regard to timely dispensing of medications or dietary supplements.

Many people take one or more medications or dietary supplements, such as minerals or vitamins, several times a day to maintain or improve their health. Often, these medications or supplements must be taken at specific times each day. If medications or supplements are not taken at the proper times, individual health may be jeopardized. For example, failure to take a prescribed medication for treatment of heart disease can result in severe health consequences such as a heart attack or stroke. Similarly, patients that seek to take extra doses before the prescribed time interval can be in danger of an overdose. Non-compliance with a prescribed dose regimen includes patients who fail to take a dose at a prescribed time or patients who take one or more extra doses that are not in compliance with the minimum time between dose of the particular prescription or label instructions for ingestion.

Further, non-compliance with a prescribed regimen of one or more medications, particularly in the elderly and the aging population of "baby boomers", can result in billions of dollars of unnecessary health care costs.

Many people who take one or more medication or supplement a day are able to take medications or supplements without assistance. However, many people who take one or more medication or supplement a day require a reminder or the assistance of a care taker. Care taker's may be one or more members of the patient's family or other individuals, such as friends, nurses, nurse's aids and the like. It can be difficult for a patient or a care taker to organize a patient's medications or supplements to insure compliance with a predetermined schedule. Further, it can be extremely difficult to monitor compliance with multiple medication schedules. Failure to properly monitor compliance can result in catastrophic health consequences to the patient and high levels of care taker anxiety, which can also lead to increased health problems for care takers.

Known pill organizers have severe limitations. One such limitation is the need to remind the patient to take their medication when the patient is away from the dispensing unit. Another such limitation is the inability for a user or a care taker to remotely monitor a patient's compliance with a medication schedule.

The present invention solves these difficult problems in a novel manner by improving the overall ease of compliance with a programmable schedule for dispensing one or more medications or supplements. Rather than requiring, for example, a dedicated alarm unit that the patient must carry with them, the instant invention is more efficient because many people already carry multifunctional interactive wireless devices (MIWDs) such as cell phones.

Interactive medicine organizers comprising multifunctional interactive wireless devices such as cell phones having programmable software that can communicate with one or more medicine dispensers and methods for monitoring and improving patient compliance with medication schedules are disclosed herein.

SUMMARY OF THE INVENTION

In one aspect of the invention an apparatus comprises a dispenser body. The body has a housing. A loading door can be connected to the housing. A tray can have one or more chambers, the tray can be connected to the housing. A dispensing door can be connected to the housing. A docking station can be connected to the housing. A multifunctional interactive wireless device can be capable of i) docking with the docking station, ii) commanding the tray to a plurality of positions, iii) commanding the loading door to a plurality of positions and iv) commanding the dispensing door to a plurality of positions. The device can execute a software application for determining a plurality of positions of the tray, the loading door, and the dispensing door based on a data set input by a user.

In one embodiment, the tray can be substantially circular.

In another embodiment, the tray can have thirty chambers.

In yet other embodiments, each of the thirty chambers can be divided into a plurality of compartments.

In some embodiments, each of the thirty chambers can be divided into three compartments.

In other embodiments, the tray can have seven chambers.

In yet other embodiments, each of the seven chambers can be divided into a plurality of compartments.

In certain embodiments, each of said seven chambers can be divided into three compartments.

In certain embodiments the multifunctional interactive wireless device is an iPhone.

In other embodiments, the data set comprises a name of a pill; a strength of the pill; and a time schedule for dispensing the pill.

In, some embodiments, the multifunctional interactive wireless device communicates an alarm to a user. The alarm can be based on a time schedule.

In still other embodiments, the multifunctional interactive wireless device can communicate a signal to a remote database. The signal indicates whether or not the contents of one or more chambers have been dispensed.

In another aspect of the present invention a method comprises 1) entering a data set into a software application. The application can be executed on a multifunctional interactive wireless device; 2) loading one or more pills into a tray. The tray can have one or more chambers; 3) docking the multifunctional interactive wireless device with a docking station; and 4) commanding a dispensing door to dispense one or more pills.

In one embodiment of this aspect, the data set comprises a name of one of more pills; a strength of the one or more pills; and a time that the one or more pills are to be dispensed.

Another embodiment comprises the step of transmitting a signal from the multifunctional interactive wireless device to a remote database. The signal can indicate either a confirmation of dispensing the one or more pills or a failure to dispense the one or more pills.

In yet another embodiment the method comprises the step of transmitting an alarm from the multifunctional interactive wireless device. The alarm can be transmitted when the one or more pills are not dispensed within a predetermined time of a scheduled dispense time.

In certain embodiments, the multifunctional interactive wireless device is an iPhone.

In some embodiments the method comprises the step of sending a signal to the remote database when a user attempts to dispense one or more pills before a predetermined time.

In certain other embodiments, the method comprises the step of locking the dispensing door when a user attempts to dispense one or more pills before a predetermined time.

In yet another aspect of the invention a system for managing patient compliance with a medication schedule comprises a multifunctional interactive wireless device having a microprocessor; a storage means for storing data on a storage medium; an arithmetic circuit configured to prepare said storage means to magnetically store selected data on said storage medium; an arithmetic logic circuit configured to retrieve information from an input file, calculate a tray position and send a signal to a motor to effectuate said tray position; an arithmetic logic circuit configured to retrieve information from an input file, calculate a dispensing door position and send a signal to a motor to effectuate said door position; an arithmetic logic circuit configured to retrieve information from an input file, calculate an alarm condition and send a signal to a effectuate said alarm condition; an arithmetic logic circuit configured to retrieve information from an input file, calculate a dispensed condition or an undispensed condition and send a signal to a server to record said dispensed condition or said undispensed condition; an arithmetic logic circuit configured to retrieve information from an input file, calculate a dispense history and display a signal indicating said dispense history for monitoring compliance with a medication schedule.

BRIEF DESCRIPTION OF THE DRAWINGS

FIG. 13 is an isometric view of a MIWD included in the interactive medicine organizer of FIG. 1 showing a screen for entering first medication time of day data.

FIG. 14 is an isometric view of a MIWD included in the interactive medicine organizer of FIG. 1 showing a screen for entering first medication special instruction data.

FIG. 23 is an isometric view of a MIWD included in the interactive medicine organizer of FIG. 1 showing a screen indicating an alert for a missed dose.

FIG. 24 is an isometric view of a MIWD included in the interactive medicine organizer of FIG. 1 showing a screen for dispensing medications.

DETAILED DESCRIPTION

As used herein, the terms pill and pills refer to any size or shape of a capsule, caplet, granule, tablet, lozenge, suppository, ampoule or any other dosage form typically used for oral nasal, dermal or rectal administration of a medication or dietary supplement or for rectal administration in the form of a suppository. The term pill or pills can include medications used for injections. The terms pill and pills may also include delivery forms typically used for topical administration, such as encapsulated and packaged liquid suspensions or emulsions, powders, creams, salves, serums, ointments and the like. The terms pill, medicine or medication may be singular or plural and are used interchangeably herein.

As used herein, the terms pill, medicine and or medication refer to prescription and over-the-counter medications, dietary supplements such as vitamins, minerals or cosmetic products. Further, the terms pill, medicine and or medication refer to any product in pill form which the user has a need or desire to use on a predetermined, scheduled basis.

Figure 3:
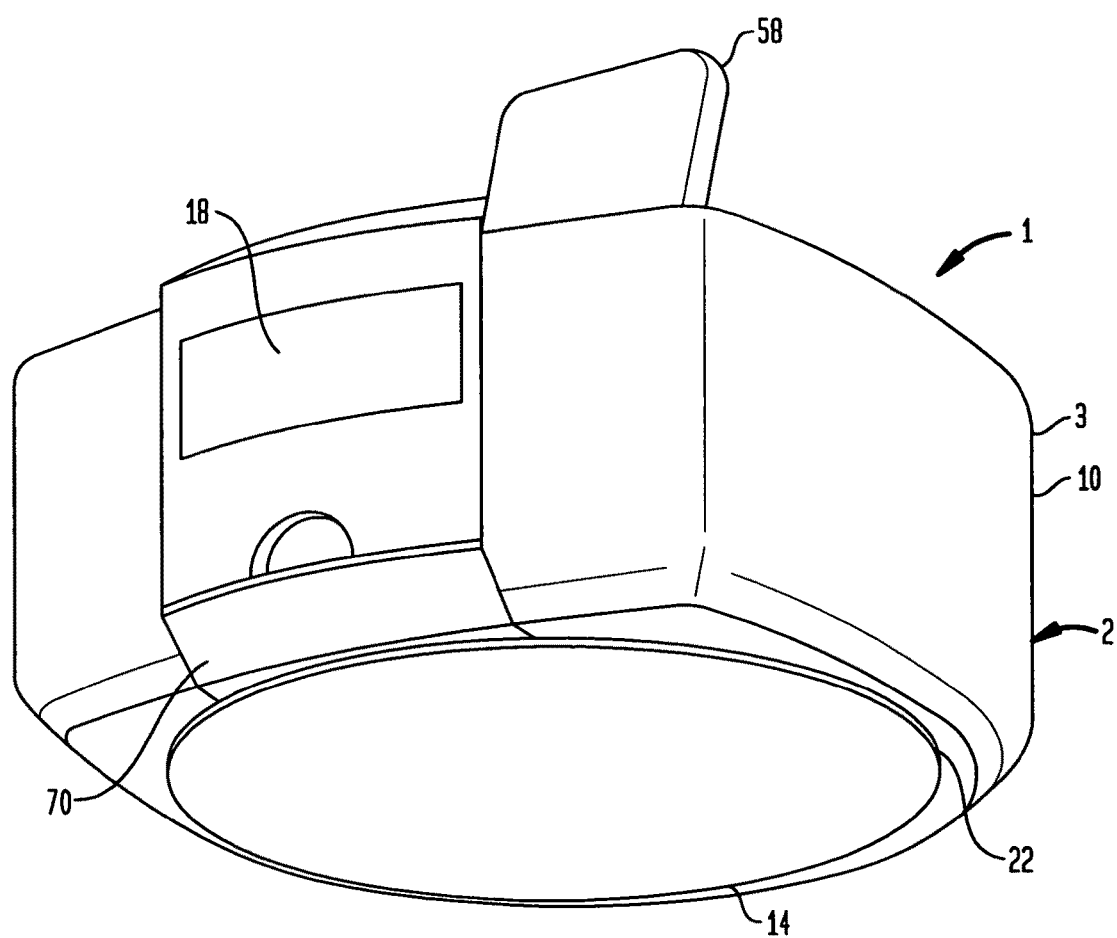
FIG. 3 is an isometric view of some of the elements included in the interactive medicine organizer of FIG. 1.

As shown in FIGS. 1-4E, interactive medicine organizer (IMO) 1 in accordance with one embodiment of the present invention includes a dispenser body 2 having a housing 3. Housing 3 has a top surface 6, side surface 10 and bottom surface 14 (FIG. 3). Housing 3 can be fabricated from plastics or other structural materials which will be known to one skilled in the art of manufacturing.

In this embodiment, an LED clock 18 is mounted to housing 3. The clock 18 can be used as a home clock or as an alarm clock. The clock 18 can also indicate, for example, the time of day, the day of the week, the date or other time related data. Clock 18 can be selected from any type of clock including digital LED devices or any other type of clock well known in the arts.

Figure 4:
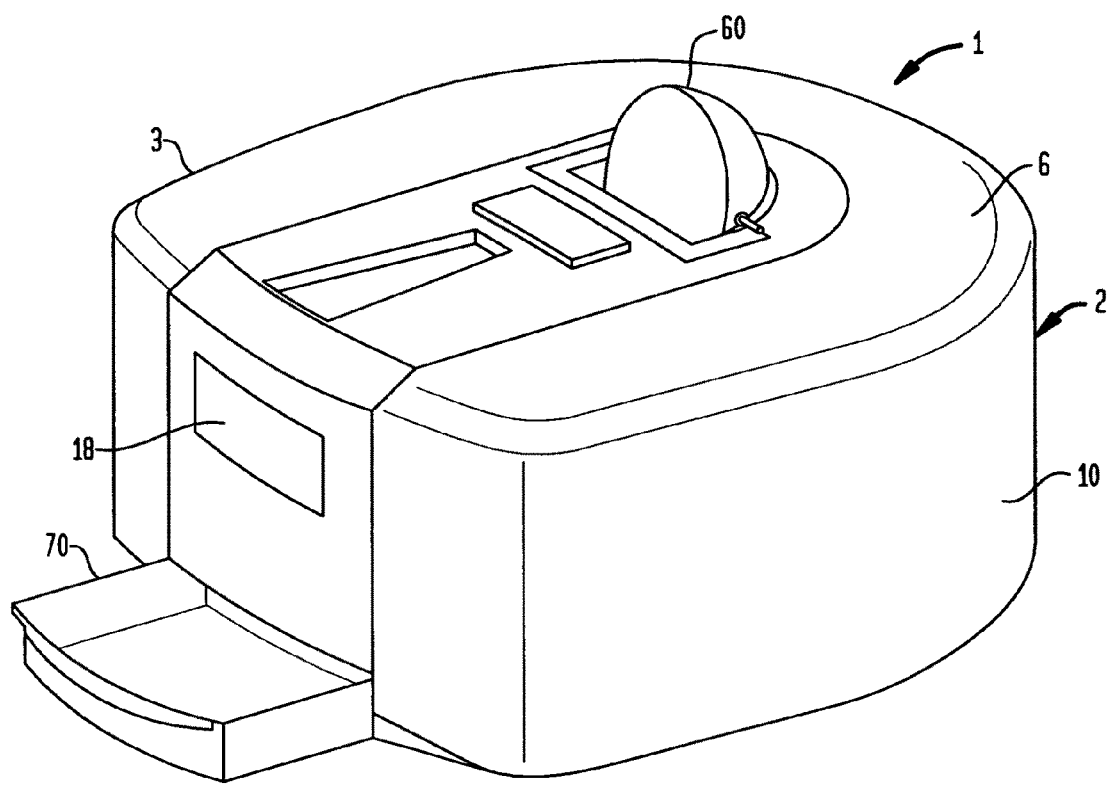
FIG. 4 is an isometric view of some of the elements included in the interactive medicine organizer of FIG. 1 showing a dispensing drawer in an open position.
Figure 4A:
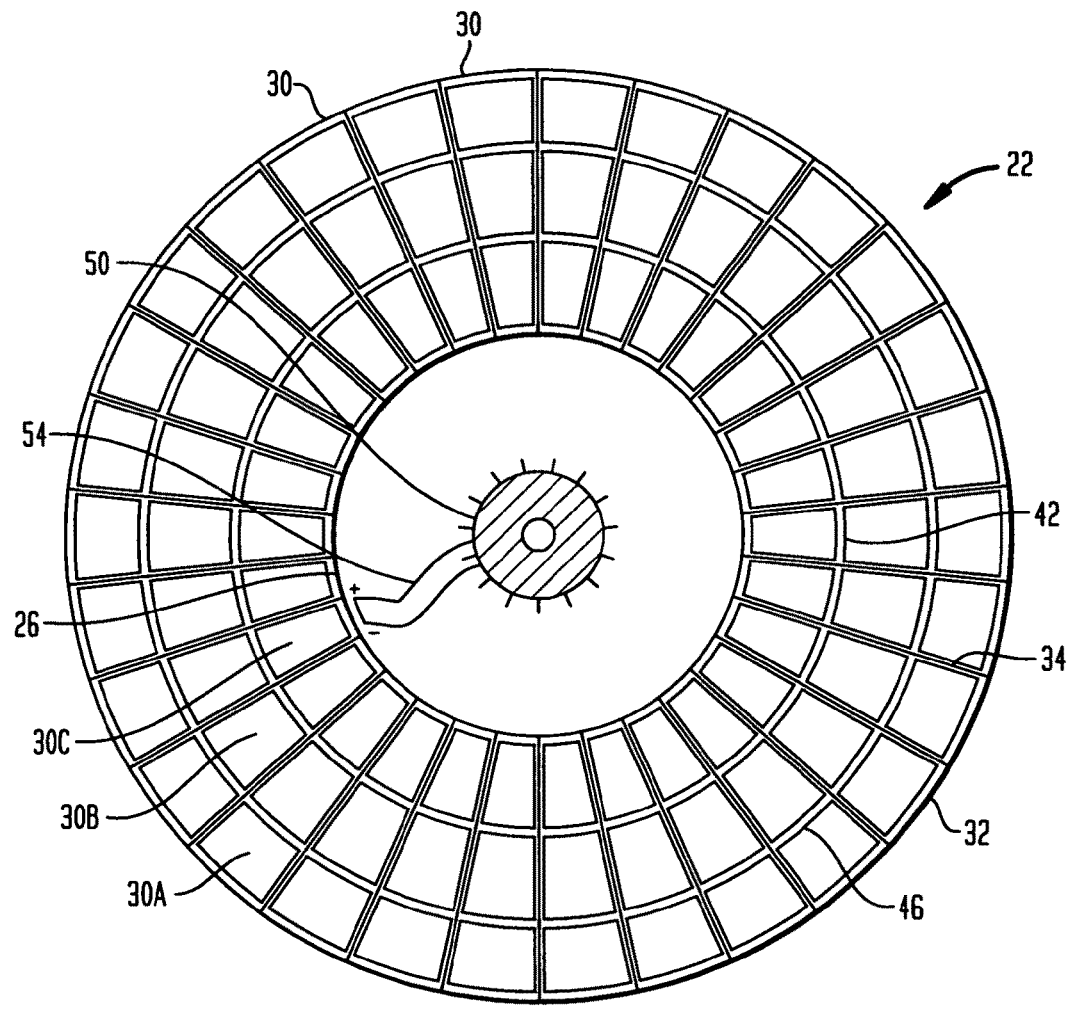
FIG. 4A is a plan view of some of the elements included in the interactive medicine organizer of FIG. 1 showing a tray and motor configuration.
Figure 4B:
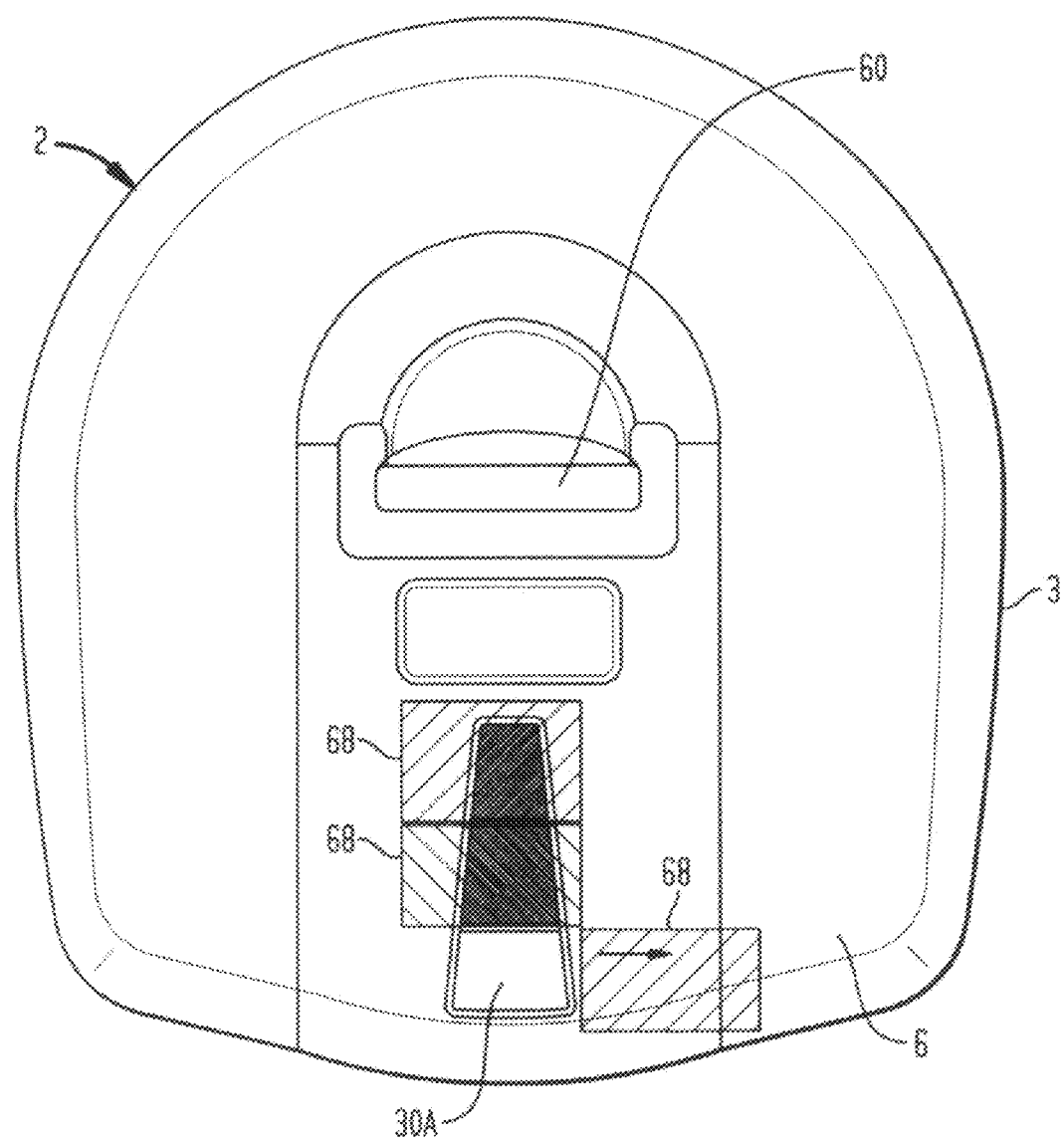
FIG. 4B is a plan view of some of the elements included in the interactive medicine organizer of FIG. 1 showing one loading configuration.
Figure 4C:
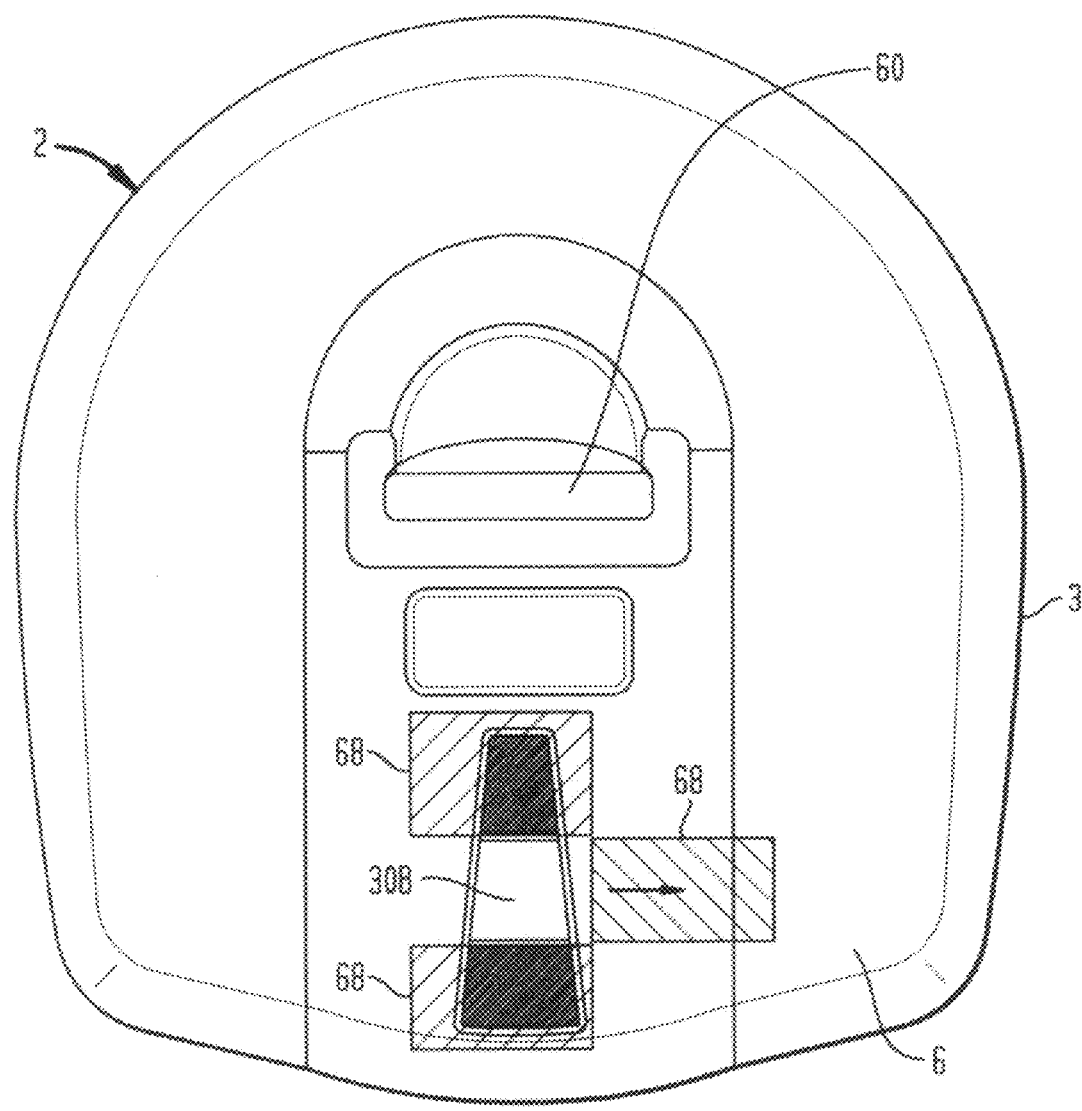
FIG. 4C is a plan view of some of the elements included in the interactive medicine organizer of FIG. 1 showing a second loading configuration.

As shown in FIG. 4A, tray 22 can be rotatably mounted within housing 3. In this embodiment, tray 22 is circularly shaped and comprises thirty (30) "daily" chambers 30, each having an inner wall 26 an outer wall 32 and side walls 34. Each daily chamber 30 is subdivided into three compartments 30A, 30B and 30C bounded by walls 26, 42, 46 and 32, respectively. Each of compartments 30A, 30B and 30C is capable of storing one or more pills. A plurality of tray geometries, chamber configurations, and compartment configurations are contemplated within the scope of the present invention. For example, a weekly tray having seven (7) daily chambers and twenty one (21) corresponding compartments is contemplated.

To facilitate loading, compartments 30A, 30B, 30C can be color coded, for example, to indicate a first color for a morning dose, a second color for an afternoon dose and a third color for an evening dose. Tray 22 can be molded or fabricated from any suitable durable structural material, for example, a polymeric material. Suitable materials and manufacturing methods will be well known to those skilled in the art.

In this particular embodiment, tray 22 is designed to hold a thirty (30) day supply of all the pills that a patient takes in a thirty day period. In this way, three doses a day are available to the patient for about a month. Each compartment can hold thirty (30) or more pills, depending on the size of the pills, thereby allowing the user to load about nine hundred pills or more into a single tray 22.

Tray 22 is indexed and controlled by electric motor 50 (FIG. 4A). Motor 50 is mechanically connected to tray 22 and electrically connected to an AC power source (not shown) through leads 54. Motor 50 is commanded by electrical signals generated by a microprocessor (not shown) in multifunctional interactive wireless device (MIWD) 58. An MIWD can be, for example, an iPhone™, a BlackBerry™, a Centro™, a PDA, an iPod™, a Droid™, or any similar touch or smart wireless or phone device. Standard motors, such as precision stepper motors, which are known to those of ordinary skill in the art can be utilized to accomplish the movement of any mechanism in the IMO that requires control or movement.

The IMO 1 can include a battery backup system (not shown) to maintain power in the event of an AC power interruption. If power is lost, all data can be stored in the MIWD (58).

Figure 1:
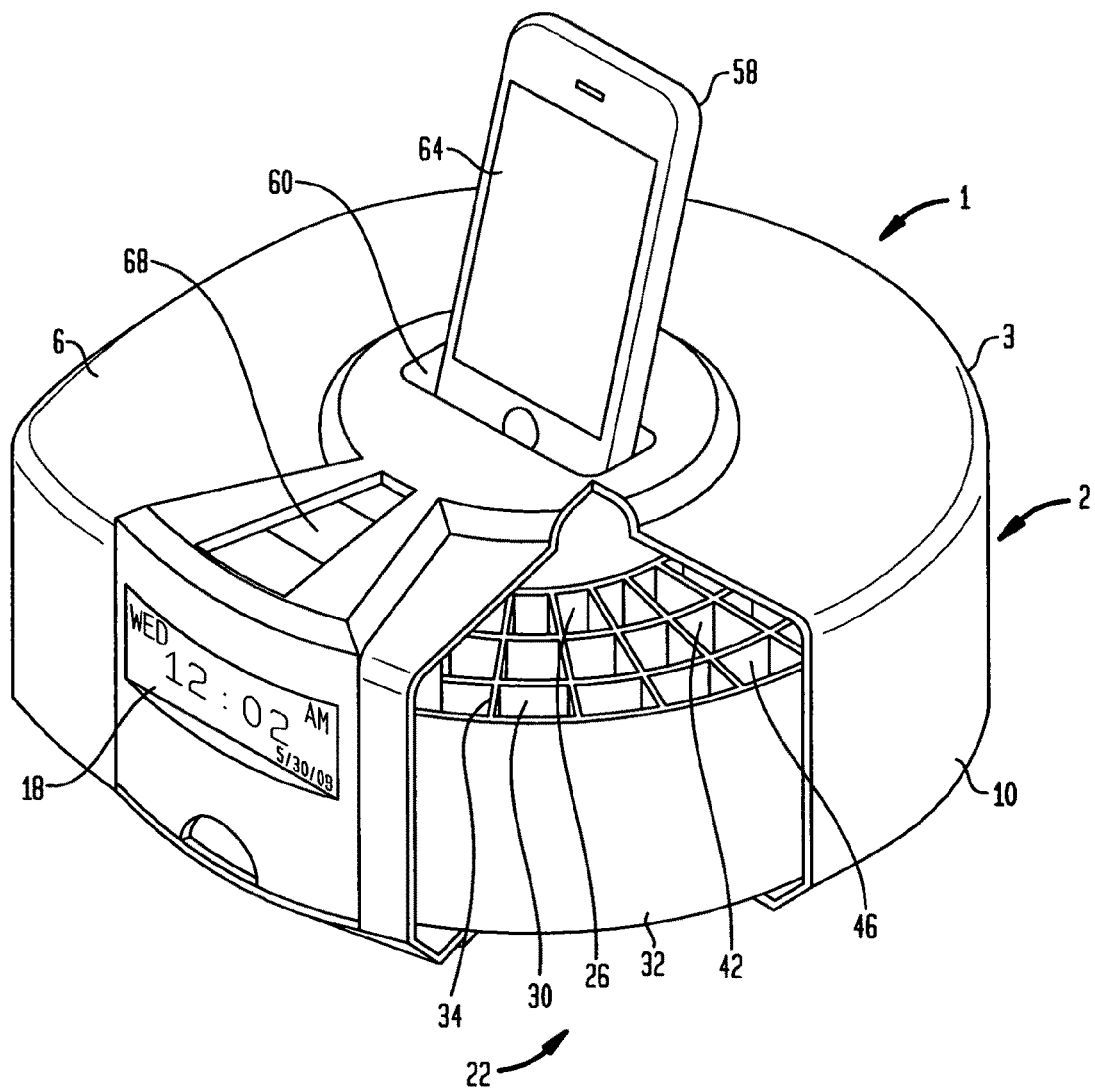
FIG. 1 is an isometric cut away view of an interactive medicine organizer according to one embodiment of the present invention in a dispensing position.
Figure 2:
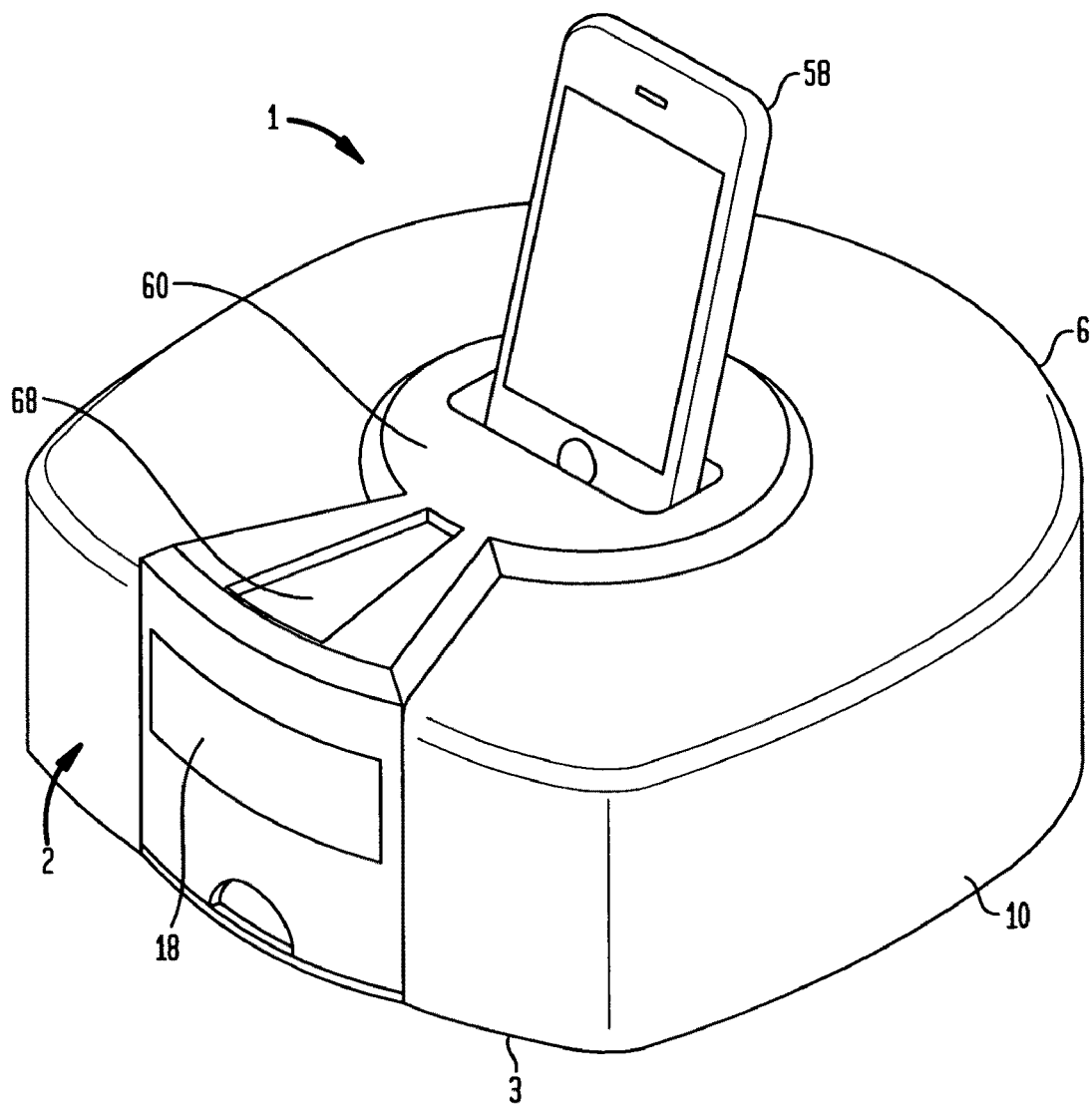
FIG. 2 is an isometric view of some of the elements included in the interactive medicine organizer of FIG. 1.

The IMO 1 further includes a docking station 60. Docking station 60 is connected to top surface 6 of housing 3. Docking station 60 is adapted to accept and connect to MIWD 58. Docking station 60 provides mechanical means to support the MIWD such that pressing on a touch screen 64 incorporated in the MIWD will not damage the IMO and will facilitate durable mechanical and electrical connectivity between MIWD 58 and dispenser body 2 (FIGS. 1, 4). The MIWD 58 mates with the docking station 60 such that the MIWD may be electrically charged or recharged through the AC power source or battery. It will be appreciated that in certain embodiments docking station 60 can comprise a wireless receiver that receives wireless signals from the MIWD and a wireless transmitter that sends wireless signals to the MIWD. In such embodiments, physical docking of the MIWD may not be necessary.

When MIWD 58 is mated to dispenser body 2 through docking station 60, MIWD 58 can send commands to cause electric motor 50 to move. Further, MIWD 58 can receive signals from the motor in order to recognize the position of tray 22 within body 2 such that the position of each compartment 30 may be commanded to any position by motor 50, thus facilitating loading or release of pills from any predetermined compartment. It will be understood that docking station 60 can include any number of adapters such that different types of MIWD can be docked. Such docking adapters and command and control algorithms between electromechanical devices are well known to those of ordinary skill in the art.

Figure 4D:
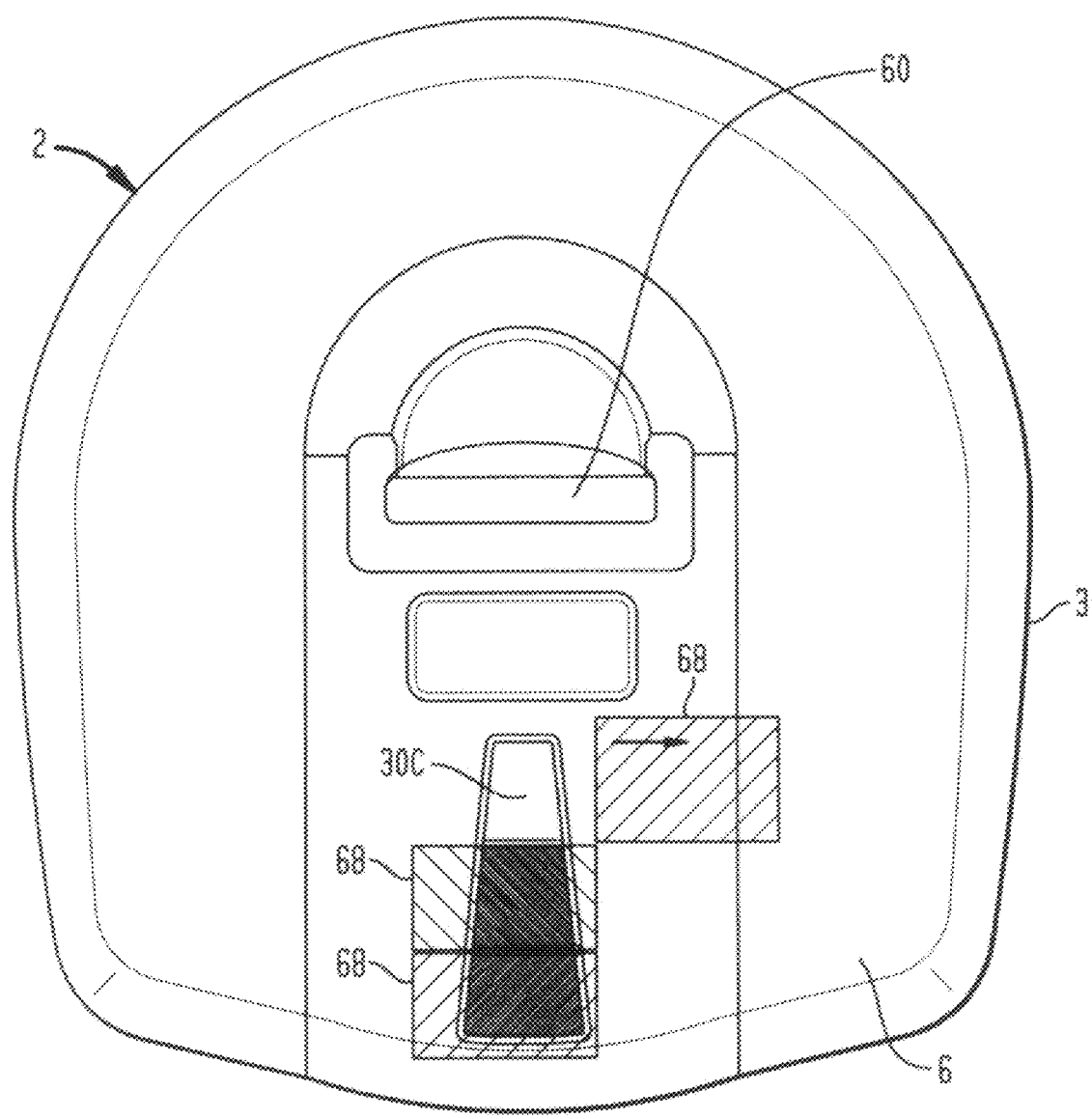
FIG. 4D is a plan view of some of the elements included in the interactive medicine organizer of FIG. 1 showing a third loading configuration.
Figure 4E:
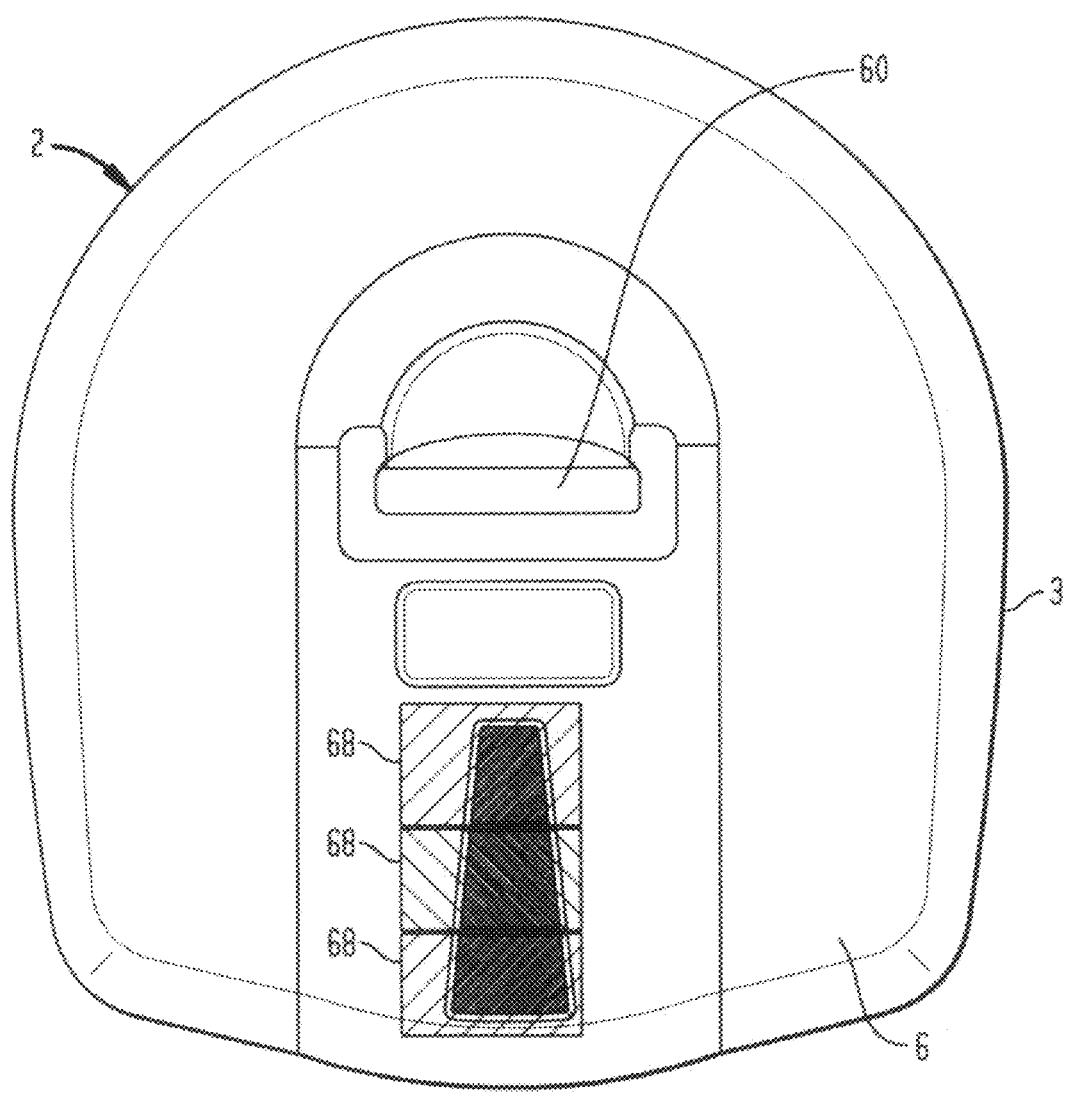
FIG. 4E is a plan view of some of the elements included in the interactive medicine organizer of FIG. 1 showing a closed configuration.

Dispenser body 2 incorporates movable loading doors 68 for loading pills into compartments 30A, 30B and 30C. As shown in FIGS. 4B-4E, loading doors 68 can be commanded by the MIWD to an open position for loading each of the compartments 30A, 30B, 30C. Each compartment can correspond with a particular dosage time frame. For example, compartment 30A can be opened for an A.M. dose (FIG. 4B), compartment 30B can be opened for a NOON dose (FIG. 4C), and compartment 30C can be opened for a P.M. dose (FIG. 4D).

Loading doors 68 can be commanded to a closed or dispensing position (FIG. 4E) in order to protect the contents of the compartments and to ensure that only the desired compartment is loaded. The loading doors are closed when the IMO is not being loaded. The loading doors can be made of a transparent material such that the contents of the compartments aligned with the loading doors are visible to the user. The loading door configuration can include other commandable mechanisms such as, for example, a rotating member with apertures spaced to facilitate an open position in which at least one compartment can be loaded or a closed position in which all compartments are closed and cannot be loaded.

In certain embodiments, the IMO includes a single loading door that overlies the housing. The door can be connected to the housing by a hinge. In operation, the loading door can be opened to expose the tray and loading compartments for loading pills. The door can be commanded by the MIWD to an open loading position or a closed or locked position.

Dispenser body 2 further includes movable dispensing doors (not shown). The dispensing doors underlie tray 22 and can operate essentially the same as the loading doors previously described.

Movement of the loading doors or the dispensing doors can be accomplished by commands sent from the MIWD. Door movement can be accomplished by any suitable mechanical system such as a motor and actuator configured to move doors to a desired position. The means for opening and closing loading or dispensing doors will be well known to a person of ordinary skill in the electro-mechanical arts. Any suitable mechanism is contemplated herein.

Drawer 70 (FIGS. 3, 4) underlies tray 22 such that when tray 22 is loaded with pills, and the proper compartment 30 is aligned over drawer 70, the MIWD 58 commands the dispensing doors to a position which allows a specific compartment to open, thus allowing the contents of any compartment (30A, 30B, 30C) to move into drawer 70. Drawer 70 can be slidably connected to housing 3 such that the user may slide drawer 70 to an open position to remove the pills and slide drawer 70 to a closed position to dispense the pills. Drawer 70 can be removed for ease of cleaning or for dispensing pills.

In operation, the IMO is controlled by a software application executed by MIWD 58. In this embodiment, the MIWD is an iPhone™, but any mobile phone or wireless device capable of running third party applications and controlling hardware can also be used. The MIWD 58 can also maintain a wireless internet connection such as, for example, 3G or WiFi technology that allows for connection to the internet. The wireless connection permits, among other things, remote monitoring of a patient's user defined medicine schedule and monitoring compliance with the schedule as will be described further below.

The user interface can have a graphical display designed for ease of use. The user can be guided through a series of steps to set up and program the IMO, dispense pills and perform other desirable functions.

Programming Example.

Figure 6:
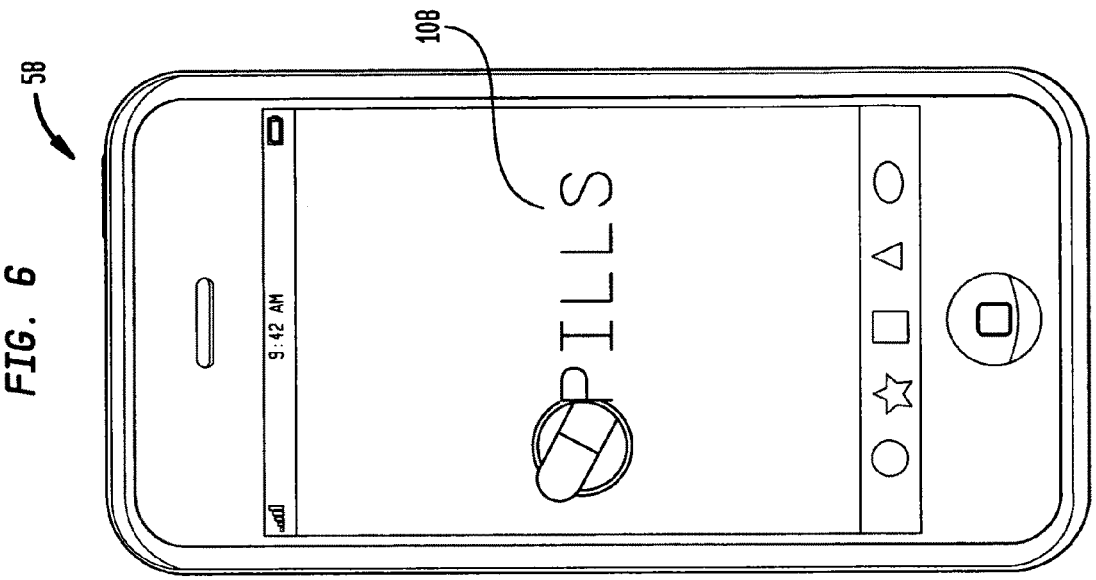
FIG. 6 is an isometric view of a MIWD included in the interactive medicine organizer of FIG. 1 showing a start up screen for accessing the organizer software application.
Figure 5:
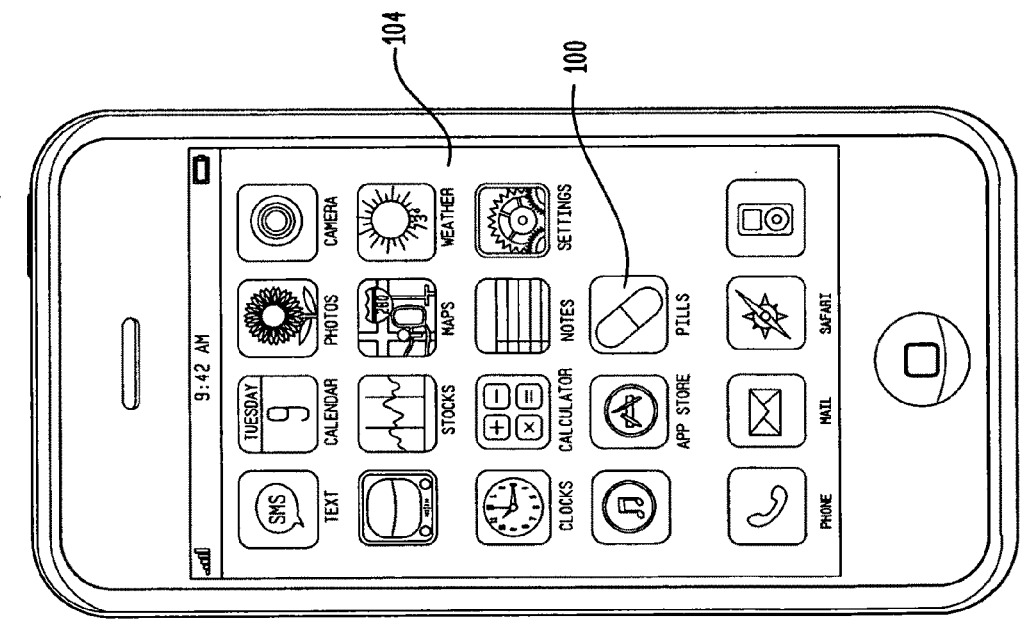
FIG. 5 is an isometric view of a MIWD included in the interactive medicine organizer of FIG. 1 showing a home screen for accessing the organizer software application.
Figure 7:
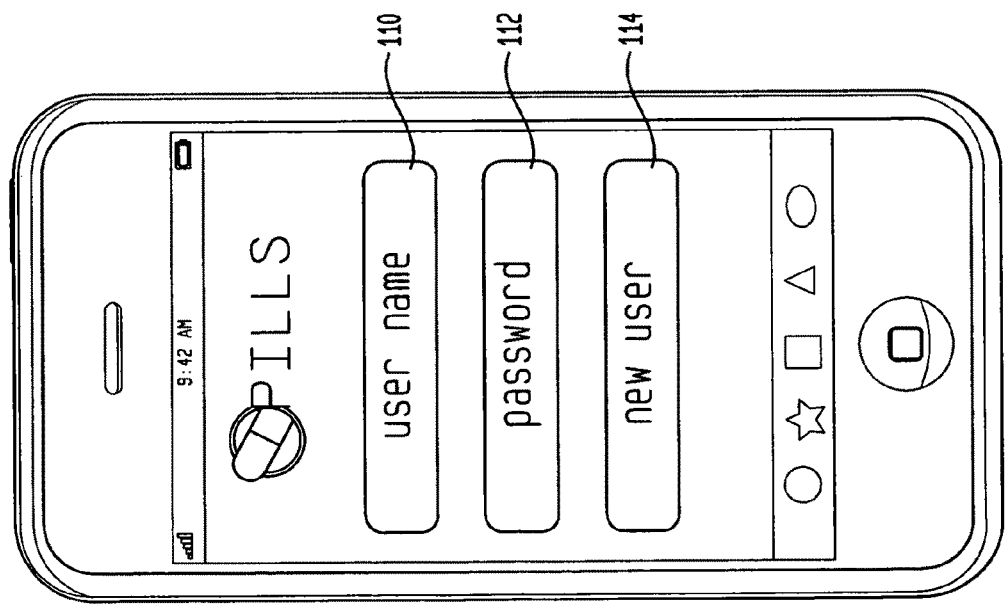
FIG. 7 is an isometric view of a MIWD included in the interactive medicine organizer of FIG. 1 showing user name, password and new user screen for accessing the organizer software application.

In one embodiment, the user can depress an icon 100 on the touch screen homepage 104 of the MIWD 58. The icon identifies the pill dispenser application (FIG. 5). When the application is loaded on the MIWD, an application identification screen, for example, "Pills" 108 is displayed (FIG. 6). Next, the user can be presented with options to enter a user name and password or set up a new user account as depicted in FIG. 7. In the event that the user is a new user 114 or desires to open a new account the user is prompted to enter a user name 110 and password 112. A secure online account can be created for each user on a remote server and linked to the MIWD by a wireless network. In the event that the user already has an account, a secure link will be created to access the user's account on a remote server.

Figure 8:
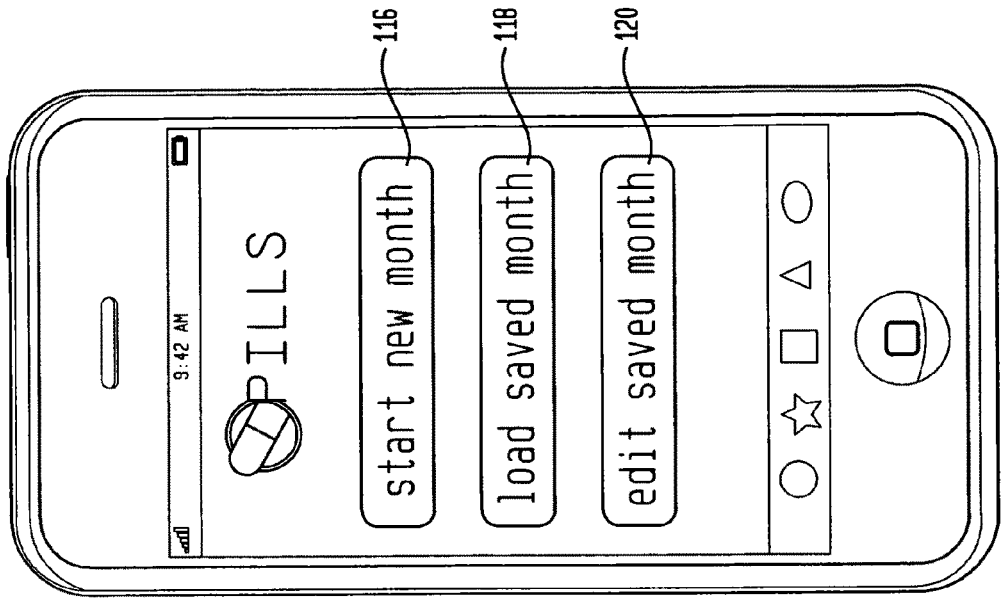
FIG. 8 is an isometric view of a MIWD included in the interactive medicine organizer of FIG. 1 showing a screen for staring, loading or editing a monthly schedule.
Figure 10:
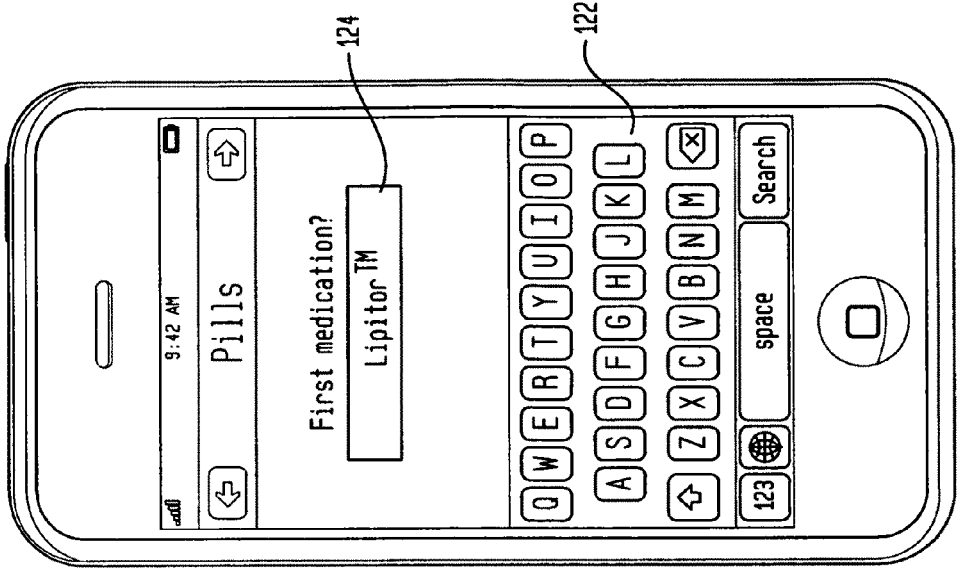
FIG. 10 is an isometric view of a MIWD included in the interactive medicine organizer of FIG. 1 showing a screen for entering first medication name data using a virtual keyboard.
Figure 9:
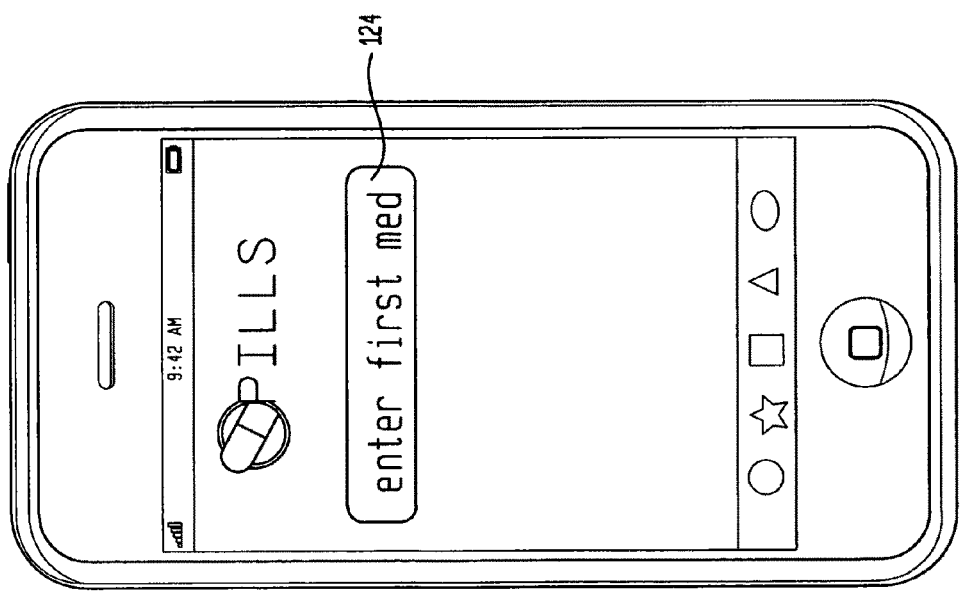
FIG. 9 is an isometric view of a MIWD included in the interactive medicine organizer of FIG. 1 showing a screen for entering first medication data.
Figure 12:
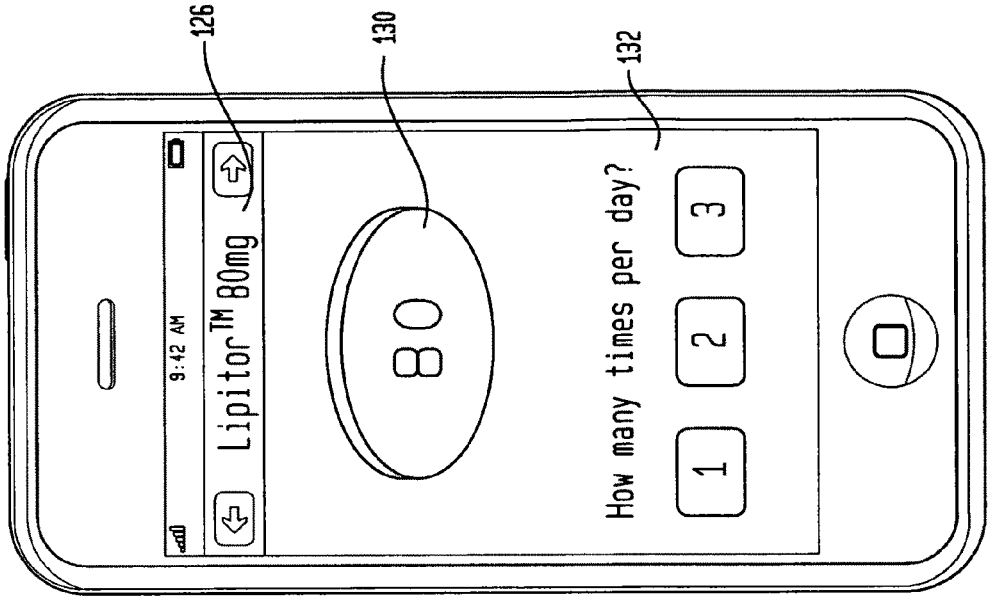
FIG. 12 is an isometric view of a MIWD included in the interactive medicine organizer of FIG. 1 showing a screen for entering first medication times per day data.
Figure 11:
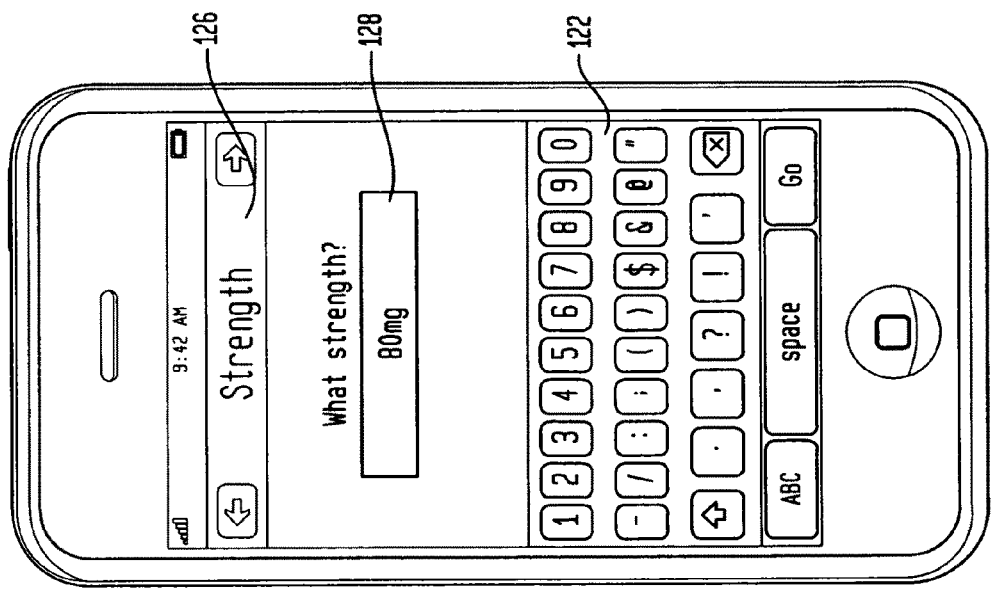
FIG. 11 is an isometric view of a MIWD included in the interactive medicine organizer of FIG. 1 showing a screen for entering first medication strength data.

As shown in FIG. 8, the user can perform one of several operations such as "start new month" 116, "load saved month" (118) or "edit saved month" 120. If the user is a first time user, the user can select "start new month" 116. The user can then enter each medication that requires dispensing. A mini-keyboard 122 can be used to type in the name of the first medication 124 (FIGS. 9, 10). Next, the user will be prompted to enter the strength 126, or dose size 128 of the medication, for example, 80 mg (FIG. 11). Once the medication name and strength or dose size is entered, subsequent screens can include a graphic depiction 130 of the actual pills (FIGS. 12, 13).

After the user enters the medicine name and strength, the user can be prompted to enter the number of times the medicine is taken per day 132, for example 1, 2, or 3, and the times of day that the medicine is to be taken 134, for example, A.M., NOON, or P.M. (FIGS. 12, 13).

As shown in FIG. 14, the next screen allows the user to enter special instructions 136 such as, for example, "take with food", "do not drink alcohol" or "do not drive or use machinery". These special instructions can act as important safety warnings at the time the medicine is dispensed.

Figure 15:
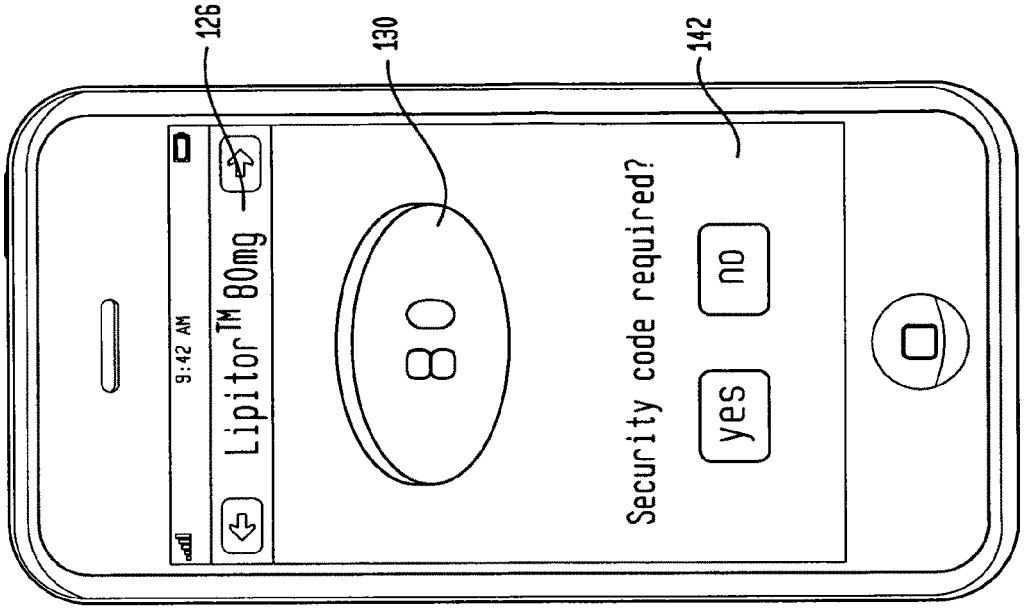
FIG. 15 is an isometric view of a MIWD included in the interactive medicine organizer of FIG. 1 showing a screen for entering prescribing doctor data.

As depicted in FIG. 15, the MIWD 58 can prompt the user to enter the prescribing doctor's or pharmacist's name 138 and phone number 140, if applicable. In the event the user has a question or experiences a problem, for example, a missed dose, the user can instantly place a call to the prescribing doctor or a pharmacist to obtain appropriate instructions.

Figure 16:
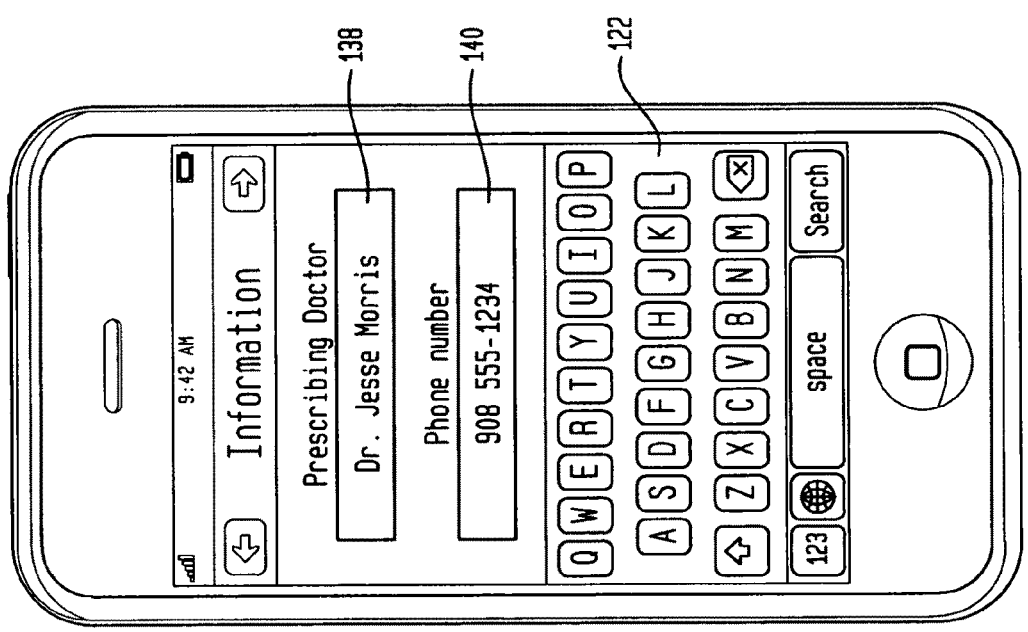
FIG. 16 is an isometric view of a MIWD included in the interactive medicine organizer of FIG. 1 showing a screen for selecting security data.
Figure 17:
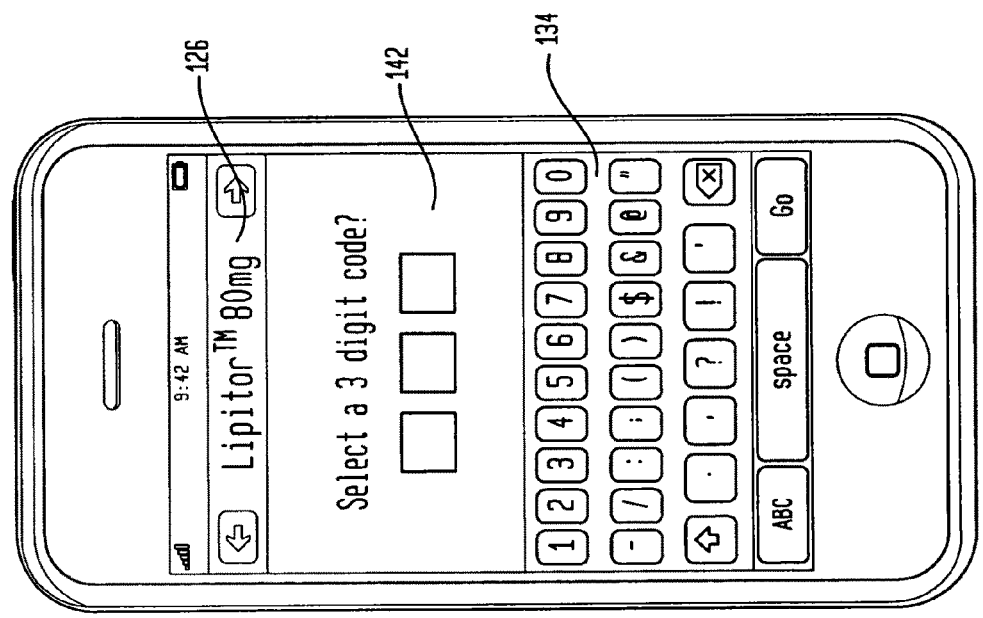
FIG. 17 is an isometric view of a MIWD included in the interactive medicine organizer of FIG. 1 showing a screen for entering security data.
Figure 20:
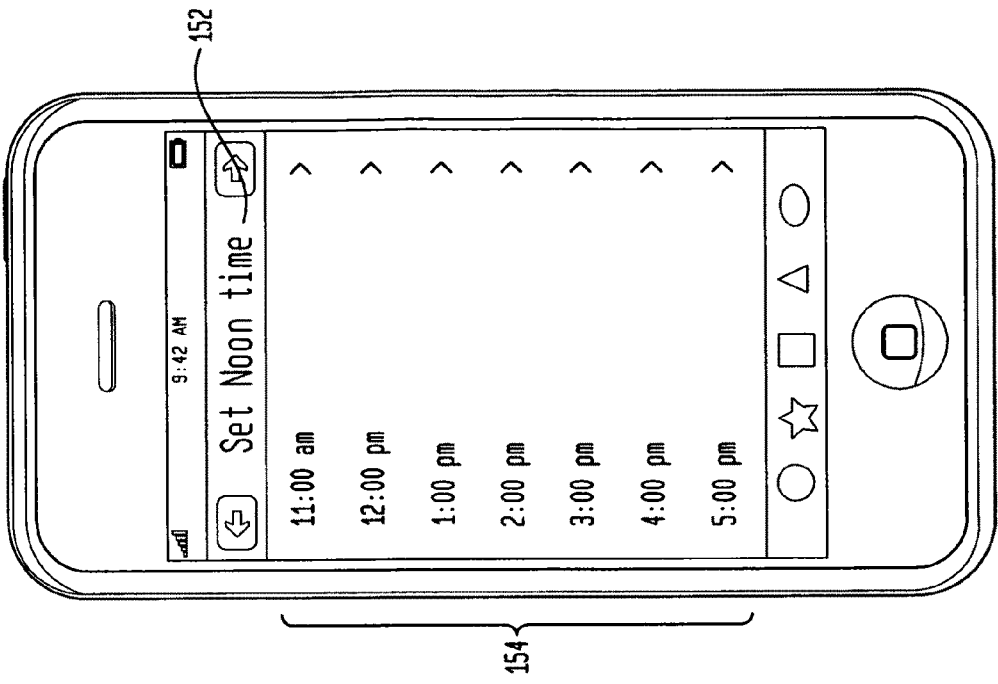
FIG. 20 is an isometric view of a MIWD included in the interactive medicine organizer of FIG. 1 showing a screen for setting a time.
Figure 19:
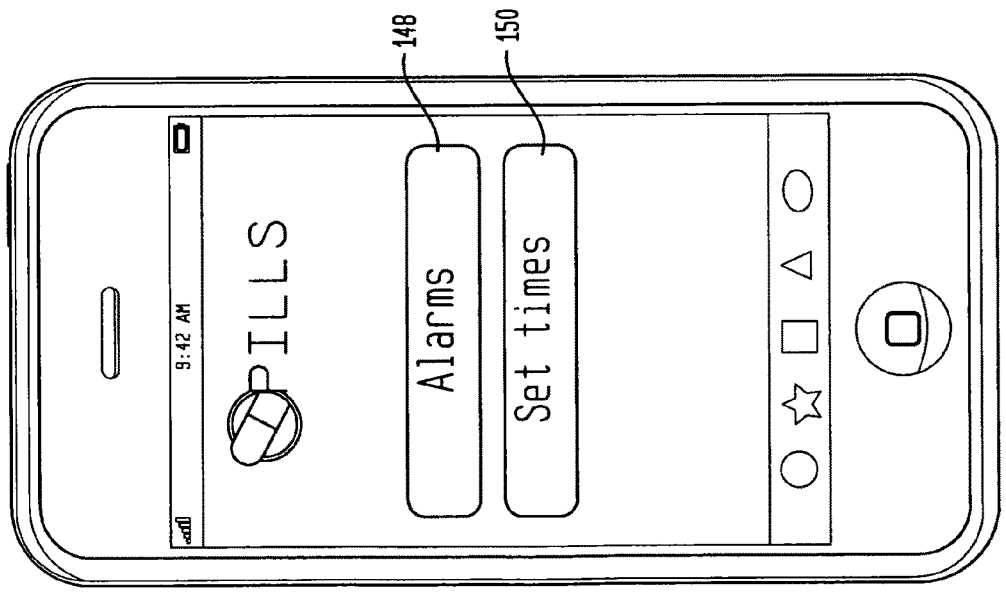
FIG. 19 is an isometric view of a MIWD included in the interactive medicine organizer of FIG. 1 showing a screen for entering time data.

If desired, the user can enter a security code 142 (FIGS. 16, 17) such that other users may not access or change the user's individual account information, for example, the security code can prevent tampering by young children in the home or prevent a patient from modifying the program to dispense pills at will. This lockout feature can be an important safety feature in preventing unauthorized dispensing off pills or potential overdose.

Figure 18:
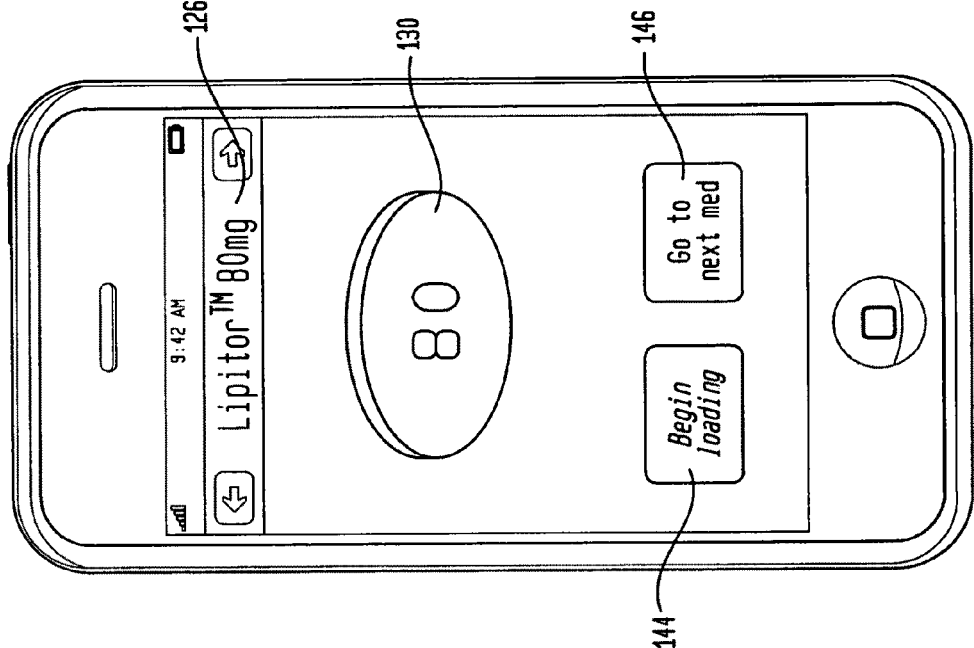
FIG. 18 is an isometric view of a MIWD included in the interactive medicine organizer of FIG. 1 showing a screen for selecting a next medication or loading option.

Next, the user can continue to enter another medication or can begin loading 144 tray 22 (FIG. 18). If "go to next med" 146 is selected, the data entry process is repeated as previously described and depicted in FIGS. 9-17. The process is repeated until all desired-medications are entered into the software application database.

Figure 22:
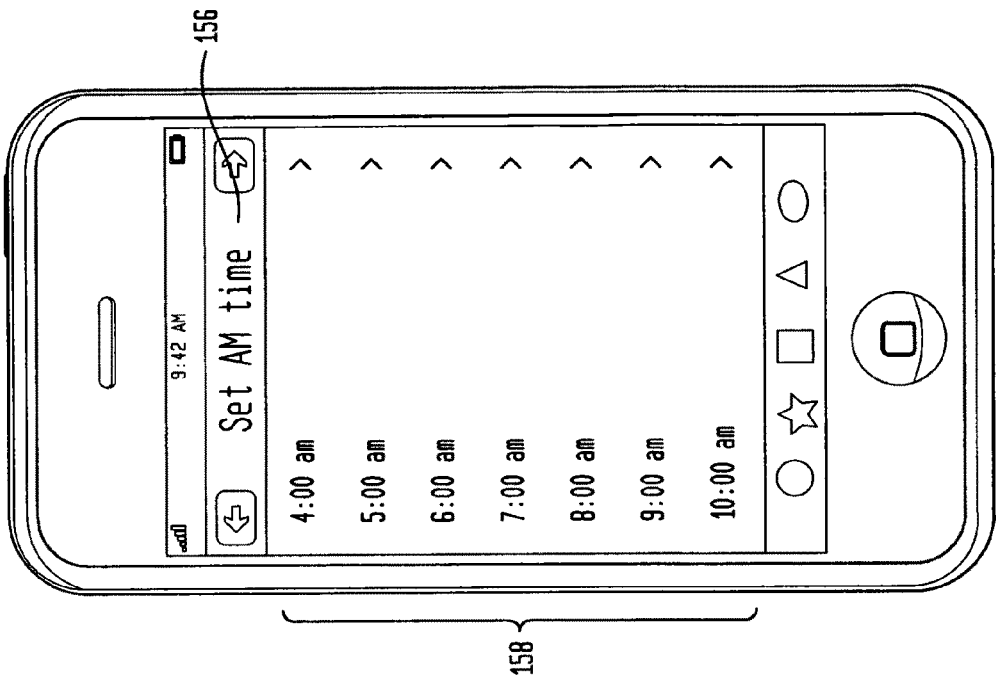
FIG. 22 is an isometric view of a MIWD included in the interactive medicine organizer of FIG. 1 showing a screen for setting an alarm.
Figure 21:
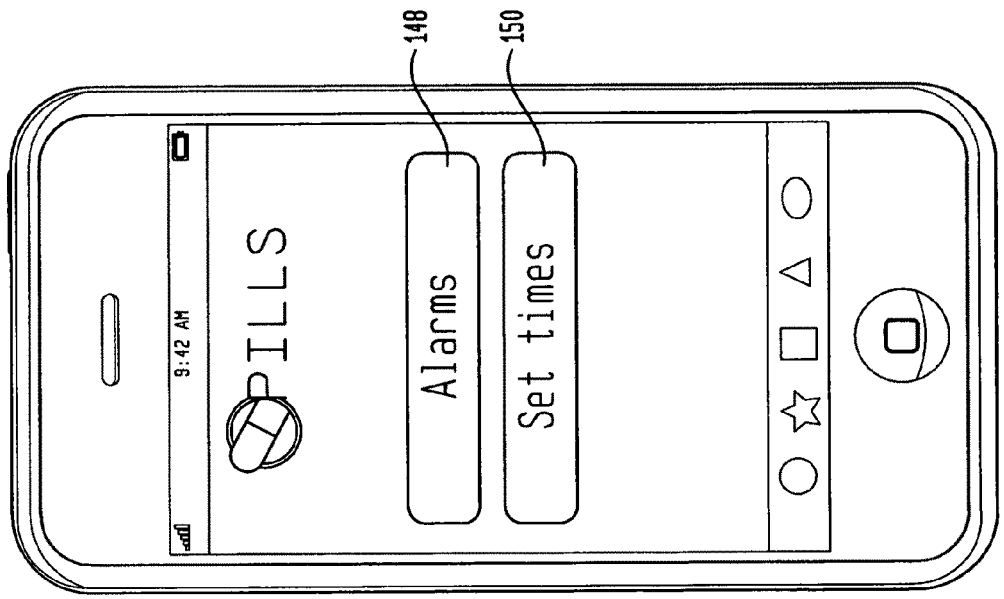
FIG. 21 is an isometric view of a MIWD included in the interactive medicine organizer of FIG. 1 showing a screen for entering alarm data.

Next, as shown in FIGS. 19-22, the application prompts the user to set alarms 148 and times 150 for each time field (AM, NOON, PM) to a specific time. The noon time alarm 152 can be set for any hour and minute 154 as shown, for example, in FIG. 20. Similarly, the AM alarm time (156) can be set to any hour and minute 158 as shown in FIGS. 21-22. The time and alarm fields can be set to any time or any number of times per day.

Loading Example.

When the user selects "begin loading" 144, (FIG. 18) the user is guided through the pill loading process. That is, the user can be instructed which pills to place in each compartment for the entire month, if desired. The "Pills" software application can guide the user visually or audibly to load each of compartments 30A, 30B and 30C with the proper pills. The software application causes the MIWD to send an electrical signal to drive the motor 50. The motor 50 rotates the tray 22 and the loading doors 68 to the proper position for each day and each time to ensure accurate loading of each chamber and compartment.

For example, when the user is prompted to load pills into a "Sunday AM" chamber of the tray, the MIWD will display the name and a picture of all medications to be loaded into the "Sunday AM" chamber. The loading doors 68 can be commanded into position such that the user can easily load the specified pills into the correct compartment and chamber (i.e. 30A, 30B, or 30C) of the tray 22. The MIWD has a microprocessor that can electrically commands the movable loading doors 68 to the proper position for each day and time by commanding motor to move the loading door mechanism to the proper position. This feature virtually eliminates the possibility of accidentally placing pills into the wrong compartments or chambers.

When the loading process is complete for "Sunday AM", the IMO will advance tray 22 to the next compartment (30A, 30B, 30C), for example, "Sunday NOON" and will display the name and images of the pills that are to be loaded into the "Sunday NOON" compartment. Again, the movable loading doors 68 are automatically positioned in place above the "Sunday NOON" compartment by interaction of the MIWD which commands the tray 22, the loading doors 68 and the dispensing doors to the proper positions. This process is repeated until all medications are loaded into the appropriate compartments in the tray.

When the tray is loaded a second time, (i.e. the next month, next week), or for all subsequent loading times, the MIWD application can save all loading sequences so that each user or user account, does not need to re-enter the medicine, dose and time information. The user can load the tray without any further programming effort. Further, the user can modify a saved schedule as needed to change any or all parameters. For example, if a user takes the same five medications each day and her doctor adds a new medication, the user can simply add the new medication to the existing schedule which has been saved in the MIWD database and the remote server database. The MIWD database and the server database can be synchronized. The MIWD application is designed to be flexible for ease of use and maximum efficiency.

Medication Time.

After the IMO is programmed and loaded with pills, the MIWD can alert 160 the user when it is time to take the appropriate medication. First, the MIWD can signal the user with a visual or audible alarm 170 or both. The audible alarm can be selected from audio files residing on the MIWD. For example, a ring tone can act as an audible alarm. At the same time, the MIWD screen can display a visual alert 162 comprising the dose time 164, an image of the pill or pills to be taken and their names 166 (FIG. 23).

To dispense the pills, the MIWD can be mated to docking station 60 of the dispenser body 2. The user can press the touch screen display area indicating "DISPENSE" 168 as shown in FIG. 24. A signal from the MIWD positions the dispensing doors, via an electromechanical positioning means such as motor 50, thereby causing the pills in the predetermined compartment to move into dispensing drawer 70. Once the pills are dispensed, the user can slide the drawer out to access the proper pills at the proper time.

As shown in FIGS. 23-24, the MIWD can enter an alert mode 160 when a dose is missed. The MIWD screen can display which medications were missed along with the dose time and images of the missed doses 166. Further, the MIWD application provides useful instructions 163 to the user regarding what to do in the event of a missed dose and provides instant access to the prescribing doctor's phone number. With a touch of the MIWD touch screen, the patient can call the prescribing doctor or dispensing pharmacist for additional advice. The MIWD can also provide internet hyperlinks to the pill manufacturer's website for additional information about each medication, for example, medication side-effects (not shown).

Monitoring and Compliance.

Figure 25:
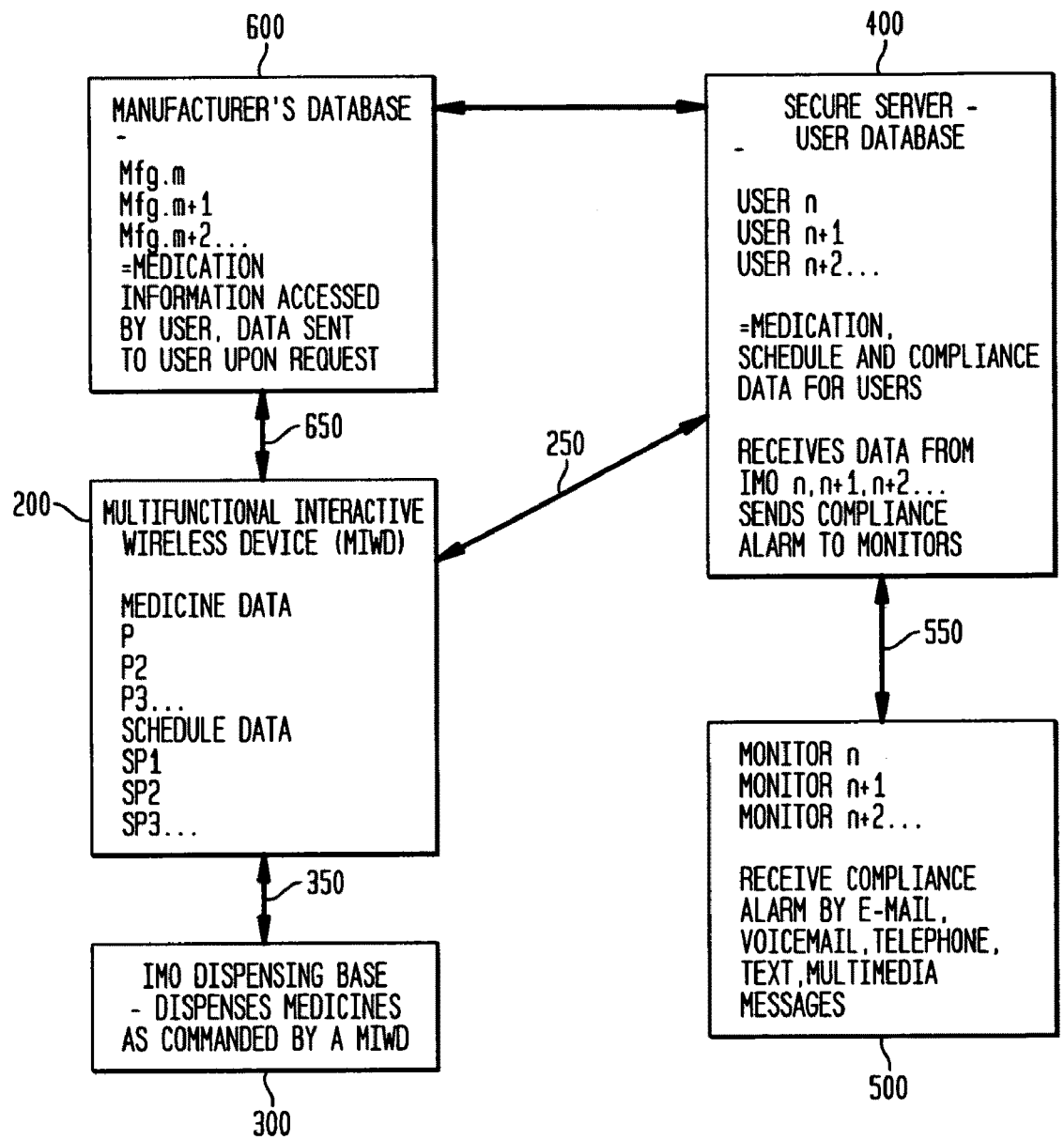
FIG. 25 is a schematic showing some of the system elements included in the interactive medicine organizer of FIG. 1.

As shown in FIG. 25, when a dose of pills, that is, the contents of a compartment is dispensed, a signal 250 is sent from the MIWD application data base 200 via a network to the user's private database 400 on secure server (not shown). The database is maintained on the MIWD 58 (not shown) and on the secure server database 400. The databases can be synchronized. The network can be a cell phone network, a WiFi network or any other type of wireless or wired network with internet connectivity. In one embodiment, the application can include the ability to communicate through a hard line network such as a cable network or fiber optics network to connect to the internet.

As discussed above, dispensing data can be communicated to the remote server database 400; the data is available for review and analysis by the user or a care taker. The data may be presented in any number of ways including charts, graphs or tables. In this way, the user's medication dispensing history can be reviewed for compliance with the desired schedule for taking the medications.

In one embodiment, the application includes a feature which alerts a care taker that a dose has not been dispensed via a signal 550 to the network. For example, application can generate a message 500 such as phone message, text message or e-mail message which can be sent directly to the user, care taker, doctor, family member or any number of interested parties. This feature can be particularly useful when, for example, a care taker or family member desires to monitor the medication dispensing compliance of a senior citizen such as a parent, family member or individual who may be suffering from a memory disorder or who may simply be forgetful. When the user receives a "missed dose" message, appropriate action can be taken in real-time to correct the short term non-compliance and address the longer term issues associated with the inability or unwillingness of a patient to comply with a medication schedule. This process is described in more detail below. Further, a similar alert can be sent when a user attempts to dispense pills too often or in a manner inconsistent with the proper medication schedule.

As illustrated above, users can input data for numerous medications into the databases 200, 400. Medication specific supplementary information can also be provided directly by a network link 650 from a manufacturer's database 600 for one or more medications. Supplementary information can include, for example, the name of the medication, its function, how and when the medication should be taken, missed dose information, information about side effects including specific actions required if the patient experiences side effects, possible interactions with other medications, and where the patient can find additional information about the medication, such as hyperlinks to the manufacturer's website. Further, manufacturers can send coupons and other desirable information such as, for example, safety alerts directly to users through the network to the IMO.

Referring to FIG. 25, the MIWD comprises a software application (app) that is programmed to store medicine and schedule data for one or more medications. The MIWD database 200 stores medicine and schedule information that is input by the user or acquired from the manufacture's database 600. The MIWD database 200 can be used to command the IMO dispensing base 300 to one or more loading positions and one or more dispensing positions by a wireless signal 350 or by a hard line electrical signal 350, for example, by docking the MIWD 58 with the docking station 60. When a dose is dispensed or missed by the user, the MIWD communicates with the secure server database 400. Server database 400 can be accessed by users having a password and a username. Authorized users can login to the database 400 to monitor patient compliance.

It is contemplated that numerous graphs and reports can be displayed or printed such that the person accessing the database 400 can easily recognize compliance problems, determine whether there are any recurring compliance problems, or print medication lists.

As previously described, database 400 can communicate with monitoring module 500. In the event of a compliance problem, for example, a missed dose of heart medication, module 500 can issue commands to send an alarm or alarms to concerned individuals by e-mail, text or other means. In this way, a care taker can be timely notified of a missed dose and can implement corrective action.

As will also be appreciated, a significant benefit of the present invention includes the ability to store the user's medicine schedule on both an MIWD that the user may carry with them and on a secure online database. A patient's medication information can be invaluable to a new doctor or in the event a user is taken to the hospital. The present invention allows a nurse, doctor, EMT or other health care professional to access a patient's medication regimen or dispensing history by accessing the server database. This feature can dramatically reduce the risk of prescribing the wrong medication and also reduce the time before necessary treatment is administered.

Although the invention herein has been described with reference to particular embodiments, it is to be understood that these embodiments are merely illustrative embodiments and that other arrangements may be devised without departing from the spirit and scope of the present invention as defined by the disclosure herein.

What is claimed is:

1. An apparatus comprising:
   (a) a dispenser body having a housing;
   (b) a loading door, said loading door being connected to said housing;
   (c) a tray, said tray having one or more chambers, said tray being connected to said housing;
   (d) a dispensing door; said dispensing door being connected to said housing;
   (e) a docking station, said docking station being connected to said housing;
   (f) a multifunctional interactive wireless device, said device being capable of i) docking with said docking station, ii) commanding said tray to a plurality of positions, iii) commanding said loading door to a plurality of positions and iv) commanding said dispensing door to a plurality of positions, wherein said device executes a software application for determining said plurality of positions of said tray, said loading door, and said dispensing door based on a data set input by a user.

2. The apparatus of claim 1, wherein said tray is substantially circular.

3. The apparatus of claim 2, wherein said tray comprises thirty chambers.

4. The apparatus of claim 3, wherein each of said thirty chambers is divided into a plurality of compartments.

5. The apparatus of claim 3, wherein each of said thirty chambers is divided into three compartments.

6. The apparatus of claim 2, wherein said tray comprises seven chambers.

7. The apparatus of claim 6, wherein each of said chambers is divided into a plurality of compartments.

8. The apparatus of claim 6, wherein each of said seven chambers is divided into three compartments.

9. The apparatus of claim 1, wherein said multifunctional interactive wireless device is an iPhone.

10. The apparatus of claim 1, wherein said data set comprises:
    (a) a name of a pill;
    (b) a strength of said pill; and
    (c) a time schedule for dispensing said pill.

11. The apparatus of claim 10, wherein said multifunctional interactive wireless device communicates an alarm to a user, said alarm being based on said time schedule.

12. The apparatus of claim 1, wherein said multifunctional interactive wireless device communicates a signal to a remote database, said signal indicating whether or not a contents of said one or more chambers have been dispensed.

* * * * *